United States Patent
Sheu et al.

(10) Patent No.: US 9,216,149 B2
(45) Date of Patent: Dec. 22, 2015

(54) SOLID, COLOR-STABLE L-ASCORBIC ACID COMPOSITIONS

(71) Applicant: DSM IP ASSETS B.V., Heerlen (NL)

(72) Inventors: Shan-Shan Sheu, Basel (CH); Jean-claude Tritsch, Basel (CH); Varaiya Chirag, Basel (CH); Salmon Clive, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/395,616

(22) PCT Filed: Apr. 18, 2013

(86) PCT No.: PCT/EP2013/058038
§ 371 (c)(1),
(2) Date: Oct. 20, 2014

(87) PCT Pub. No.: WO2013/156543
PCT Pub. Date: Oct. 24, 2013

(65) Prior Publication Data
US 2015/0141503 A1 May 21, 2015

Related U.S. Application Data

(60) Provisional application No. 61/636,037, filed on Apr. 20, 2012.

(51) Int. Cl.
| | |
|---|---|
| A61K 8/67 | (2006.01) |
| A23L 1/302 | (2006.01) |
| A23K 1/16 | (2006.01) |
| A23L 1/00 | (2006.01) |
| A23L 1/272 | (2006.01) |
| A61K 8/37 | (2006.01) |
| A61K 8/36 | (2006.01) |
| A61K 8/73 | (2006.01) |
| A61Q 19/00 | (2006.01) |
| A61K 8/92 | (2006.01) |
| A61K 8/02 | (2006.01) |

(52) U.S. Cl.
CPC ............... *A61K 8/676* (2013.01); *A23K 1/1603* (2013.01); *A23L 1/0026* (2013.01); *A23L 1/272* (2013.01); *A23L 1/302* (2013.01); *A61K 8/0225* (2013.01); *A61K 8/361* (2013.01); *A61K 8/37* (2013.01); *A61K 8/375* (2013.01); *A61K 8/731* (2013.01); *A61K 8/922* (2013.01); *A61Q 19/00* (2013.01); *A23V 2002/00* (2013.01); *A61K 2800/10* (2013.01); *A61K 2800/30* (2013.01); *A61K 2800/92* (2013.01)

(58) Field of Classification Search
CPC ........................................................ A61K 8/676
USPC ........................................... 549/474; 514/474
See application file for complete search history.

(56) References Cited

U.S. PATENT DOCUMENTS

| | | | |
|---|---|---|---|
| 5,141,758 A | 8/1992 | Monte | |
| 5,234,702 A * | 8/1993 | Katz et al. | 426/72 |
| 2011/0217410 A1 | 9/2011 | Perlman | |
| 2012/0156296 A1* | 6/2012 | Torgersen et al. | 424/478 |

FOREIGN PATENT DOCUMENTS

| | | |
|---|---|---|
| WO | WO 95/28084 | 10/1995 |
| WO | WO 2005/110123 | 11/2005 |

OTHER PUBLICATIONS

International Search Report for PCT/EP2013/058038 mailed Aug. 1, 2013.
Written Opinion of the International Searching Authority mailed Aug. 1, 2013.

* cited by examiner

*Primary Examiner* — Taofiq A Solola
(74) *Attorney, Agent, or Firm* — Nixon & Vanderhye P.C.

(57) ABSTRACT

The present invention relates to solid, color-stable L-ascorbic acid compositions, which are in the form of a powder or granule. These improved compositions have a high amount of vitamin C and they have excellent color stability.

13 Claims, 1 Drawing Sheet

SOLID, COLOR-STABLE L-ASCORBIC ACID COMPOSITIONS

Figure 1:
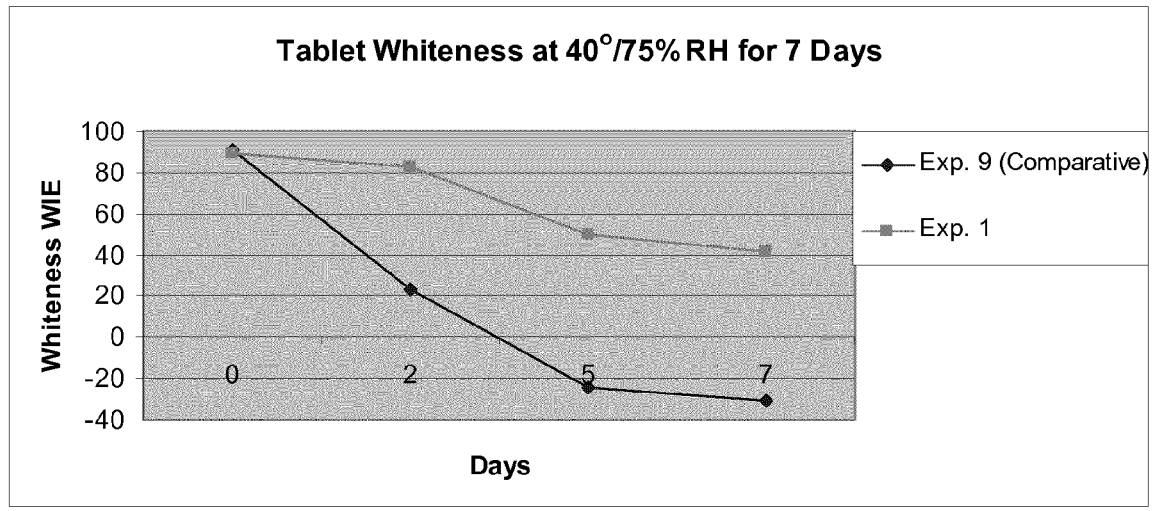

This application is the U.S. national phase of International Application No. PCT/EP2013/058038 filed 18 Apr. 2013 which designated the U.S. and claims priority to U.S. Provisional Application No. 61/636,037, filed 20 Apr. 2012, the entire contents of each of which are hereby incorporated by reference.

Provided herein are solid, color-stable L-ascorbic acid compositions, which are in the form of a powder or granule. These compositions may provide a high amount of vitamin C and may additionally have excellent color stability, particularly when used in a compressed tablet.

L-ascorbic acid is known per se. Many salts of L-ascorbic acid are also known. One of the most common one is the sodium ascorbate. There are numerous forms of granulated forms of vitamin C for high potency tabletting applications such as C90, C95, C97, and Sodium Ascorbate 99% from DSM Nutritional Products.

L-ascorbic acid and sodium ascorbate are both white and odorless solids. Sodium ascorbate can be synthesized from ascorbic acid. L-ascorbic acid can be produced on an industrial scale i.e. by the Reichstein process.

Crystalline L-ascorbic acid is stable if protected from humidity, but is somewhat sensitive to heat. Sodium ascorbate is somewhat sensitive to air, heat, and humidity. A stability issue of L-ascorbate acid is that when it is exposed to moisture the white shade gets darker. This is a problem for the products such as i.e. tablets, capsules, etc which comprise L-ascorbic acid and/or salts thereof.

An incompatible factor in high dosage ascorbic acid tablets is the commonly used lubricant, magnesium stearate. Such a formulation develops yellowish shade and loses its whiteness already during a short storage period.

Surprisingly, it has been found out that when the ascorbic acid composition (powder or granule) comprises a specific lubricant (or a mixture of lubricants) and suitable binder(s), the color-stability is increased (especially when used in a tablet).

In some embodiments, ascorbyl palmitate as well as ascorbyl palmitate (as lubricants), in combination with at least one specific lubricant, may provide color-stable high potency ascorbic acid tablets.

In some embodiments, ascorbyl palmitate as well as the mixture of ascorbyl palmitate with at least one specific lubricant does not affect the tablet physical properties including the compression profile and disintegration time (DT) while the ejection force is comparable.

Therefore provided herein is a composition (I) in the form of a powder or a granule comprising:
 (a) 75 weight-% (wt-%)-99 wt-%, based on the total weight of the powder or granule, of L-ascorbic acid and/or a salt thereof,
 (b) 0.1 wt-%-10 wt-%, based on the total weight of the powder or granule, of ascorbyl palmitate or of a mixture of ascorbyl palmitate and at least one compound chosen from the group consisting of hydrogenated vegetable oil, glyceryl behenate, glyceryl monostearate, glyceryl palmitostearate, stearic acid, palmitic acid, myristic acid, talc, sodium lauryl sulfate, waxes, sodium stearyl fumarate, and polyethylene glycol, and
 (c) 0.9 wt-%-10 wt-%, based on the total weight of the powder or granule, of at least one binder, and
 (d) optionally adjuvants in quantities within the range of 0.05 wt-%-5 wt-%, based on the total weight of the powder or granule, with the proviso that the composition is essentially free from magnesium stearate.

These compositions, which can be used as such or in suitable formulations, such as tablets, may provide improved color-stability when exposed to stress conditions for example at high moisture and/or high temperature conditions.

All percentages are always added up to 100.

A particular composition (II) is a composition (I), wherein sodium ascorbate is used. Function of a binder is that it holds the ingredients in a solid composition (such as a granule or tablet) together. Binders may ensure that granules and tablets can be formed with required mechanical strength, and give volume to low active dose tablets with good homogeneity of content.

Binders provided herein may comprise (especially suitable for granulation purpose) saccharides and their derivatives, proteins and synthetic polymers. A particularly group of saccharides provided herein comprises:
 Di-saccharides, such as sucrose and lactose,
 Polysaccharides and their derivatives, such as gum arabic, tragacanth, pectin and starches,
 sugar alcohols, such as xylitol, sorbitol or maltitol.

A particular group of protein provided herein comprises a gelatine (i.e. fish, pork, beef).

A particular group of the synthetic polymers provided herein comprises i.e. polyvinylpyrrolidone (PVP, povidone) and polyethylene glycol (PEG), methyl- or ethyl cellulose or modified cellulose (such as sodium carboxylmethylcellulose), polyvinyl alcohol, and cellulose ethers such as hydroxypropyl cellulose (HPC).

Further provided herein are suitable binders (especially suitable for tableting purpose) comprising microcrystalline cellulose, silicified microcrystalline cellulose, hydroxypropyl cellulose, starch, lactose, dicalcium phosphate, sucrose, dextrose, and sugar alcohols.

Some of the binders can be suitable for granulation as well as for tabletting.

A particular composition provided herein is composition (Ill), which is a composition (I) and/or (II), wherein the binder is chosen from the group consisting of saccharides and their derivatives, proteins, synthetic polymers, microcrystalline cellulose, silicified microcrystalline cellulose, hydroxypropyl cellulose, starch, lactose, dicalcium phosphate, sucrose, dextrose, and sugar alcohols.

A further embodiment provided herein is a composition (IV) in the form of a powder or a granule comprising
 (a) 84 wt-%-99 wt-%, based on the total weight of the powder or granule, of L-ascorbic acid and/or a salt thereof,
 (b) 0.1 wt-%-8 wt-%, based on the total weight of the powder or granule, of ascorbyl palmitate or of a mixture of ascorbyl palmitate and at least one compound chosen from the group consisting of hydrogenated vegetable oil, glyceryl behenate, glyceryl monostearate, glyceryl palmitostearate, stearic acid, palmitic acid, myristic acid, talc, sodium lauryl sulfate, waxes, sodium stearyl fumarate, and polyethylene glycol and
 (c) 0.9 wt-%-8 wt-%, based on the total weight of the powder or granule, of at least one binder, and
 (d) optionally adjuvants in quantities within the range of 0.05 to 5% by weight, calculated to the total weight of the composition, with the proviso that the composition is essentially free from magnesium stearate.

A particular embodiment provided herein is composition (V), which is a composition (I), (II), (III) and/or (IV), wherein the binder is chosen from the group consisting saccharides and their derivatives, proteins, synthetic polymers, microcrystalline cellulose, silicified microcrystalline cellulose, hydroxypropyl cellulose, HPC, starch, lactose, dicalcium phosphate, sucrose, dextrose, and sugar alcohols.

A powder or a granule provided herein can be produced using commonly known processes, such as fluidized-bed granulation, high-shear granulation, extrusion, spraydrying or other dry or wet granulation process.

A powder or a granule provided herein can be used as such or it can be further processed. When further processed, it can be pressed into a tablet. It can be pressed into tablet as such or together with auxiliaries commonly used in tablet pressing.

The content of L-ascorbic acid and/or a salt of powder or granule thereof, in a tablet may comprise 80 wt-%-99 wt-%, particularly 84-99 wt-%, more particularly 90-99 wt-%, based on the total weight of the tablet.

In some embodiments, the content of ascorbyl palmitate in a tablet is 0.3 wt-%-5 wt-%, based on the total weight of the tablet.

In some embodiments, the content of stearic acid in a tablet is 0.3 wt-%-5 wt-%, based on the total weight of the tablet.

In some embodiments, the content of binder (preferably microcrystalline cellulose, silicified microcrystalline cellulose, hydroxypropyl cellulose, HPC, starch, lactose, dicalcium phosphate, sucrose, dextrose, and/or sugar alcohols) in a tablet is 0.5 wt-%-8 wt-%, based on the total weight of the tablet.

A powder or the granule provided herein n as well as any further processed form can be used as such or in combination with further ingredients in dietary supplement, food, feed or personal care formulation.

Therefore also provided herein is the use of at least one composition (I), (II), (Ill) and/or (IV) in a dietary supplement, food, feed or personal care formulation.

Therefore also provided herein is a dietary supplement, food, feed or personal care formulation comprising at least one composition (I), (II), (Ill), (IV) and/or (V).

FIG. 1: Color Stability Data of Example 9 (Comparative Example) and Example 1 (Invention) of tablet in open tray at 40° C./75% RH for 7 days. Color of tablets was measured using HunterLab Colorimeter on WIE. FIG. 1 shows the values of the Whiteness (WIE).

Figure 2:
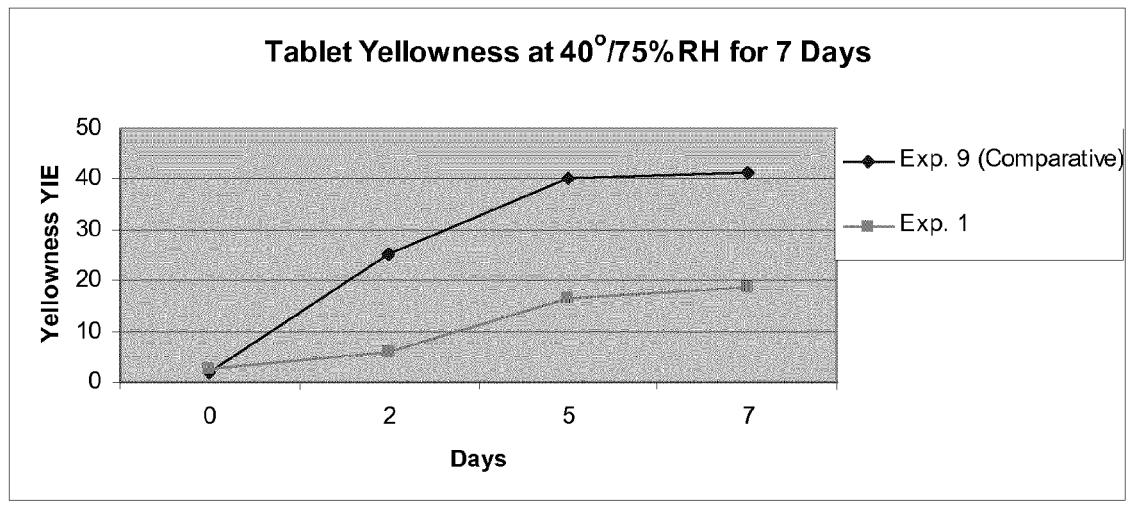

FIG. 2: Color Stability Data of Example 9 (Comparative Example) and Example 1 (Invention)) of tablet in open tray at 40° C./75% RH for 7 days. Color of tablets was measured using HunterLab Colorimeter on YIE values. FIG. 2 shows the values of the Yellowness (YIE).

The following examples serve to illustrate specific embodiments of the invention claimed herein. All percentages are given in relation to the weight and all the temperatures are given in degree Celsius.

EXAMPLES

All of the examples have been prepared according to the following process:

The ascorbic acid (in form of a 97% granulation, commercially available from DSM) was put in a blender. Afterwards the microcrystalline cellulose (MCC 102) and the silicon dioxide (Cab-O-Sil®) were sieved through a 20 mesh and also transferred to the blender. Afterwards the stearic acid and the ascorbyl palmitate were sieved through a 30 mesh and also transferred to the blender. This blend was mixed for 10 minutes and the discharged in a container.

Example 1

| Ingredients | g | wt-% |
| --- | --- | --- |
| Ascorbic Acid (97%) | 1031 | 91.24 |
| Microcrystalline Cellulose | 70.75 | 6.26 |
| Stearic Acid | 16.95 | 1.50 |
| Ascorbyl Palmitate | 11.30 | 1.00 |

Example 2

| Ingredients | g | wt-% |
| --- | --- | --- |
| Ascorbic Acid (97%) | 1031 | 91.24 |
| Microcrystalline Cellulose | 76.40 | 6.76 |
| Silicon Dioxide | 5.65 | 0.50 |
| Stearic Acid | 11.30 | 1.00 |
| Ascorbyl Palmitate | 5365 | 0.50 |

Example 3

| Ingredients | g | wt-% |
| --- | --- | --- |
| Ascorbic Acid (97%) | 1031 | 91.24 |
| Microcrystalline Cellulose | 70.75 | 6.26 |
| Silicon Dioxide | 5.65 | 0.50 |
| Stearic Acid | 11.30 | 1.00 |
| Ascorbyl Palmitate | 11.30 | 1.00 |

Example 4

| Ingredients | g | wt-% |
| --- | --- | --- |
| Ascorbic Acid (97%) | 1031 | 91.24 |
| Microcrystalline Cellulose | 65.10 | 5.76 |
| Silicon Dioxide | 5.65 | 0.50 |
| Stearic Acid | 11.30 | 1.00 |
| Ascorbyl Palmitate | 16.95 | 1.50 |

Example 5

| Ingredients | g | wt-% |
| --- | --- | --- |
| Ascorbic Acid (97%) | 1031 | 91.24 |
| Microcrystalline Cellulose | 59.45 | 5.26 |
| Silicon Dioxide | 5.65 | 0.50 |
| Stearic Acid | 11.30 | 1.00 |
| Ascorbyl Palmitate | 22.60 | 2.00 |

Example 6

| Ingredients | g | wt-% |
| --- | --- | --- |
| Ascorbic Acid (97%) | 1031 | 91.24 |
| Microcrystalline Cellulose | 53.80 | 4.76 |
| Silicon Dioxide | 5.65 | 0.50 |
| Stearic Acid | 11.30 | 1.00 |
| Ascorbyl Palmitate | 28.25 | 2.50 |

Example 7

| Ingredients | g | wt-% |
| --- | --- | --- |
| Ascorbic Acid (97%) | 1031 | 91.24 |
| Microcrystalline Cellulose | 48.15 | 4.26 |
| Silicon Dioxide | 5.65 | 0.50 |
| Stearic Acid | 11.30 | 1.00 |
| Ascorbyl Palmitate | 33.90 | 3.00 |

Example 8

| Ingredients | g | wt-% |
| --- | --- | --- |
| Ascorbic Acid (97%) | 1031 | 91.24 |
| Microcrystalline Cellulose | 67.93 | 6.01 |
| Silicon Dioxide | 2.83 | 0.25 |
| Stearic Acid | 16.95 | 1.50 |
| Ascorbyl Palmitate | 11.30 | 1.00 |

Example 9

Comparative Example

| Ingredients | g | wt-% |
| --- | --- | --- |
| Ascorbic Acid (97%) | 1082.5 | 94.75 |
| Microcrystalline Cellulose | 40.00 | 3.5 |
| Polyvinylpyrrolidone (PVP XL) | 14.00 | 1.23 |
| Magnesium Stearate | 6.00 | 0.52 |

One advantage over the prior art lies therein that the tablets pressed from the examples disclosed above are more humidity and heat stable than those of the prior art. For that purpose, the compositions of Example 1 and Example 9 have been used to pressed tablets and they have been tested in regard to whiteness and yellowness. The tablets have been stored for 7 days in open tray at 40° C./75% RH (relative humidity). Color of tablets was measured using HunterLab Colorimeter on WIE and YIE values. Visually, after 7 days, the tablet consisting of the prior art formulation turned to brown, whereas the whiteness of the tablet comprising the formulation according to the present invention did not decrease so much.

The invention claimed is:

1. A composition in the form of a powder or granules comprising:
 (a) 75 wt-%-99 wt-%, based on total weight of the powder or granules, of L-ascorbic acid and/or sodium ascorbate,
 (b) 0.1 wt-%-10 wt-%, based on the total weight of the powder or granule, of ascorbyl palmitate or a mixture of ascorbyl palmitate and at least one compound selected from the group consisting of hydrogenated vegetable oil, glyceryl behenate, glyceryl monostearate, glyceryl palmitostearate, stearic acid, palmitic acid, myristic acid, talc, sodium lauryl sulfate, waxes, sodium stearyl fumarate, and polyethylene glycol,
 (c) 0.9 wt-%-10 wt-%, based on the total weight of the powder or granules, of at least one binder, and
 (d) optionally adjuvants in quantities within the range of 0.05 wt-%-5 wt-%, based on the total weight of the powder or granule, with the proviso that the composition is essentially free from magnesium stearate.

2. The composition according to claim 1, wherein the binder is selected from the group consisting saccharides, proteins, synthetic polymers, microcrystalline cellulose, silicified microcrystalline cellulose, hydroxypropyl cellulose, starch, lactose, dicalcium phosphate, sucrose, dextrose, and sugar alcohols.

3. The composition according to claim 1, which is a powderous or granular product obtained by a granulation process slected from the group consisting of fluidized-bed granulation, high-shear granulation, extrusion, spray-drying and wet granulation.

4. A tablet which comprises a compressed powderous or granular composition according to claim 1.

5. The tablet according to claim 4, wherein component (a) comprises L-ascorbic acid and/or sodium ascorbate in an amount of 80 wt-%-99 wt-%, based on total weight of the tablet.

6. The tablet according to claim 4, wherein component (b) comprises ascorbyl palmitate in an amount of 0.3 wt-%-5 wt-%, based on total weight of the tablet.

7. The tablet according to claim 4, wherein component (b) comprises stearic acid in an amount of 0.3 wt-%-5 wt-%, based on total weight of the tablet.

8. The tablet according to claim 4, wherein component (c) comprises the at least one binder in an amount of 0.5 wt-%-8 wt-%, based on the total weight of the tablet.

9. The tablet according to claim 4, wherein the tablet is color-stable after being placed in an open tray at 40° C. and 75% relative humidity for 7 days.

10. A tablet comprising a compressed powderous or granular composition consisting essentially of, based on total tablet weight:
 (a) 75 wt-%-99 wt-% of L-ascorbic acid;
 (b) 0.1 wt-%-10 wt-% of a mixture of ascorbyl palmitate and stearic acid; and
 (c) 0.9 wt-%-10 wt-% a cellulose binder, wherein the tablet is color-stable after being placed in an open tray at 40° C. and 75% relative humidity for 7 days.

11. The tablet of claim 10, wherein the cellulose binder is microcrystalline cellulose.

12. The tablet of claim 11, wherein the composition further consists essentially of silicon dioxide.

13. A food, feed or personal care formulation comprising the composition according to claim 1.

* * * * *